United States Patent
O'Heeron et al.

(10) Patent No.: US 12,404,494 B2
(45) Date of Patent: Sep. 2, 2025

(54) PREVENTION OF RECURRENT MISCARRIAGES THROUGH ADMINISTRATION OF FIBROBLASTS AND FIBROBLAST-EDUCATED PATERNAL CELLS

(71) Applicant: SPINALCYTE LLC, Houston, TX (US)

(72) Inventors: Pete O'Heeron, Houston, TX (US); Thomas Ichim, San Diego, CA (US)

(73) Assignee: SPINALCYTE, LLC, Houston, TX (US)

(*) Notice: Subject to any disclaimer, the term of this patent is extended or adjusted under 35 U.S.C. 154(b) by 380 days.

(21) Appl. No.: 17/754,812

(22) PCT Filed: Oct. 14, 2020

(86) PCT No.: PCT/US2020/055642
§ 371 (c)(1),
(2) Date: Apr. 13, 2022

(87) PCT Pub. No.: WO2021/076675
PCT Pub. Date: Apr. 22, 2021

(65) Prior Publication Data
US 2023/0167410 A1 Jun. 1, 2023

Related U.S. Application Data

(60) Provisional application No. 62/915,292, filed on Oct. 15, 2019.

(51) Int. Cl.
*C12N 5/077* (2010.01)
*A61P 15/06* (2006.01)
*C12N 5/0783* (2010.01)

(52) U.S. Cl.
CPC ............ *C12N 5/0656* (2013.01); *A61P 15/06* (2018.01); *C12N 5/0636* (2013.01);
(Continued)

(58) Field of Classification Search
CPC .................................................. C12N 5/0656
See application file for complete search history.

(56) References Cited

U.S. PATENT DOCUMENTS

| 7,491,388 B1 | 2/2009 | McIntosh et al. |
| 2010/0150862 A1 | 6/2010 | Devergne |

(Continued)

OTHER PUBLICATIONS

International Search Report and Written Opinion issued in International Application No. PCT/US2020/055642, 13 pages, mailed Feb. 4, 2021.

(Continued)

*Primary Examiner* — Mark L Shibuya
(74) *Attorney, Agent, or Firm* — Norton Rose Fulbright US LLP

(57) ABSTRACT

Embodiments of the disclosure include methods and compositions related to prevention of spontaneous miscarriage in an individual. In certain cases, fibroblasts are provided in an effective amount to an individual in need thereof. Alternatively or in addition, lymphocytes are obtained, cultured with fibroblasts, and provided to an individual. Fibroblasts may modulate an immune response in an individual, thereby reducing the risk of spontaneous miscarriage.

22 Claims, 1 Drawing Sheet

(52) U.S. Cl.
CPC ...... *C12N 2501/10* (2013.01); *C12N 2501/20* (2013.01); *C12N 2501/22* (2013.01); *C12N 2501/40* (2013.01)

(56) References Cited

U.S. PATENT DOCUMENTS

2015/0306180 A1\* 10/2015 Scarpellini .............. A61P 15/06
                                                      424/85.1
2017/0354686 A1    12/2017 Ichim et al.

OTHER PUBLICATIONS

Liu et al., "Low-dose lymphocyte immunotherapy rebalances the peripheral blood Th/TH2/Treg paradigm in patients with unexplained recurrent miscarriage," Reproductive Biology and Endocrinology, vol. 15, Article No. 5, pp. 1-7, Dec. 16, 2017.
Hajipour et al., "Lymphocytes immunotherapy for preserving pregnancy: Mechanisms and Challenges," Am J Reprod Immunol, Mar. 2018, 80(3), 14 pages.
Office Communication issued in European Patent Application No. 20875762.5, dated Oct. 18, 2023.

\* cited by examiner

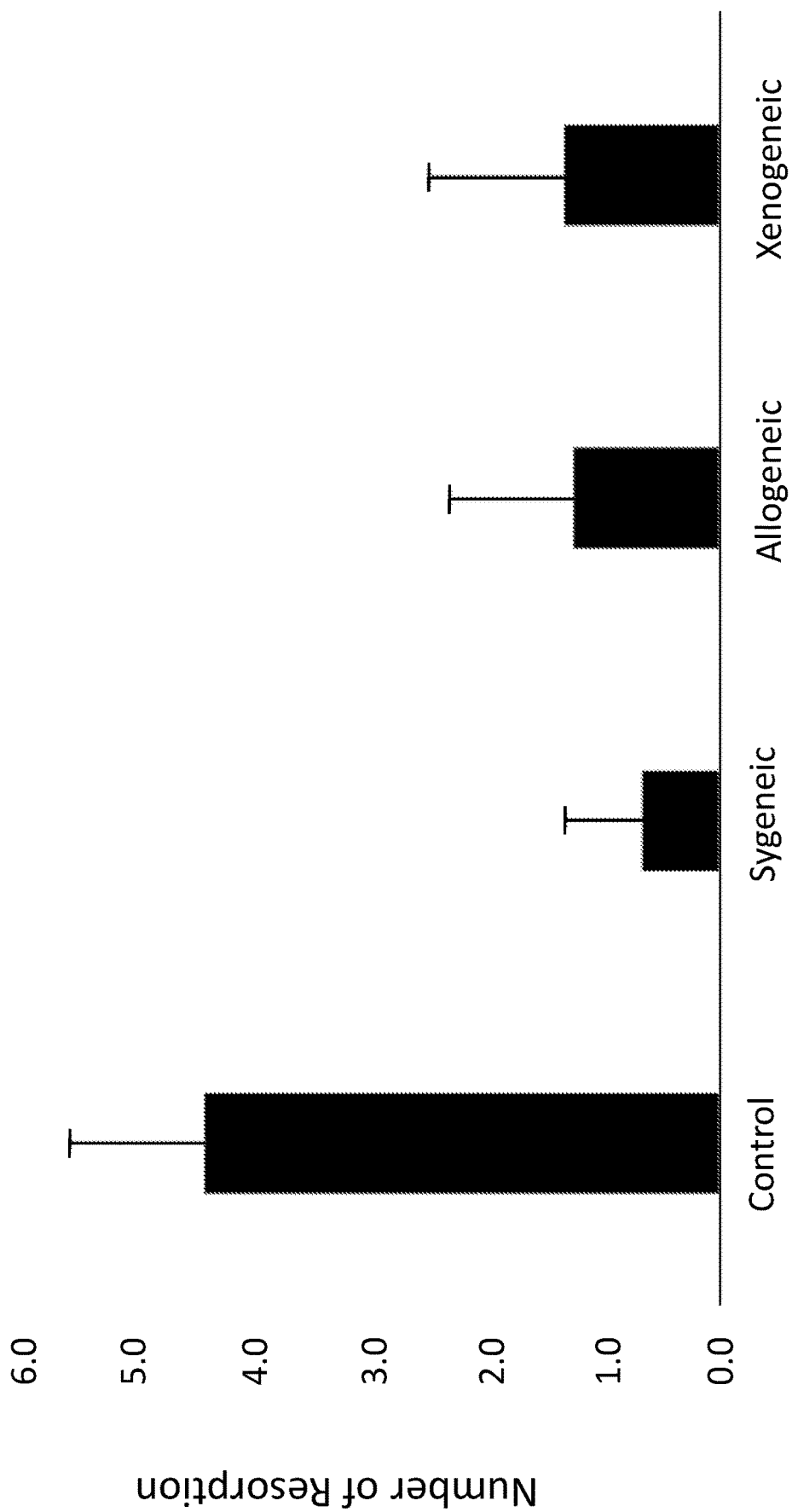

PREVENTION OF RECURRENT MISCARRIAGES THROUGH ADMINISTRATION OF FIBROBLASTS AND FIBROBLAST-EDUCATED PATERNAL CELLS

This application is a national phase application under 35 U.S.C. § 371 that claims priority to International Application No. PCT/US2020/055642, filed Oct. 14, 2020, which claims priority to U.S. Provisional Patent Application Ser. No. 62/915,292, filed Oct. 15, 2019, both of which are incorporated by reference herein in their entirety.

TECHNICAL FIELD

Embodiments of the disclosure include at least the fields of cell biology, immunology, and medicine.

BACKGROUND

Recurrent spontaneous miscarriage, or recurrent spontaneous abortion (RSA), is a complication of pregnancy that may affect as many as 2% of women in their reproductive age. More than 50% of these cases seem to be mediated by enhanced immunity to the semialloantigen fetoplacental unit. This immunity appears to correlate with Th1, Th17, and other inflammatory mechanisms. This enhanced immunity results in an abnormal immune reaction against the fetus, resulting in spontaneous abortions. During normal pregnancy in healthy individuals, maternal tolerance develops to the fetus by regulatory T cells. In patients with RSA, this tolerance does not develop. In some of these cases this lack of tolerance may result in a spontaneous abortion. Tolerance to the paternal antigens in RSA patients can be enhanced by paternal leukocyte immunization, which has been shown to significantly increase the live birth rate in RSA patients. One method for treating immunological RSA is lymphocyte immunotherapy. This immunotherapy of RSA has been used internationally since Taylor and Faulk infused to a patient of unexplained RSA a suspension of mixed leukocytes derived from her spouse in 1981[1]. The immunogen is lymphocytes from the spouse in most cases. The immunotherapy includes isolating lymphocytes from the spouse's venous blood for intracutaneous injection. Alternatively, the condensed leucocytes or whole blood from the spouse can also be intravenously injected. If the live cells are inactivated by 200 rad X-ray radiation prior to intracutaneous injection, the graft-versus-host reaction can be attenuated. Usually, the immunization is performed every 2 weeks for a total of 2 to 4 times before pregnancy and boosted 1 to 3 times after pregnancy. Twenty years after the application of lymphocyte immunotherapy for treating RSA, a great deal of studies have indicated that the therapeutic effect of this therapy is not definite in some patients and the therapy can possess adverse side effects [2].

The present disclosure satisfies a long felt need in the art for methods and compositions for modulating the immune system of females at risk for RSA to reduce miscarriages in a consistent and reproducible manner.

BRIEF SUMMARY

The disclosure pertains to the field of immunotherapy, more specifically, the disclosure relates to the field of reducing immunologically mediated miscarriages through immune modulation of the mother. The disclosure relates to means of using fibroblasts to alter immune profiles in mothers at risk of pregnancy loss.

In particular embodiments, prevention of spontaneous miscarriage is disclosed. In some embodiments, provided herein is a method of preventing spontaneous miscarriage in an individual, the method comprising providing to the individual an effective amount of fibroblasts. Peripheral blood mononuclear cells (PBMCs) of the individual may have increased interleukin-18 (IL-18), interferon gamma (INF-gamma), or tumor necrosis factor alpha (TNF-alpha) expression relative to a control. In some cases, PBMCs from the individual have increased natural killer (NK) cell activity relative to a control. The individual may have a reduced T regulatory (T-reg) cell activity relative to a control.

In some embodiments, the fibroblasts are derived from the individual. In some embodiments, the fibroblasts are not derived from the individual. In some embodiments, the fibroblasts are naturally occurring fibroblasts. The fibroblasts may be cultured under one or more conditions prior to providing the fibroblasts to the individual. For example, fibroblasts may be cultured with one or more mitogenic factors and/or under hypoxic conditions prior to being provided to the individual. In some embodiments, the fibroblasts express one or more markers selected from the group consisting of Oct-4, Nanog, Sox-2, KLF4, c-Myc, Rex-1, GDF-3, LIF receptor, CD105, CD117, CD344 and Stella. In some embodiments, the fibroblasts do not express a marker selected from the group consisting of MHC class I, MHC class II, CD45, CD13, CD49c, CD66b, CD73, CD105, and CD90.

In some embodiments, fibroblasts and/or lymphocytes are cultured prior to being provided to the individual. Fibroblasts and/or lymphocytes may be cultured with one or more growth factors. In some embodiments, fibroblasts and/or lymphocytes are cultured with IGF, EGF, VEGF, FGF-1, FGF-2, FGF-5, TGF-beta, oxytocin, GDF-11, or a combination thereof. Fibroblasts and/or lymphocytes may be cultured with one or more immune modulating agents. In some embodiments, fibroblasts and/or lymphocytes are cultured with interferon gamma, interferon beta, interferon alpha, TNF-α, IL-10, IL-35, or a combination thereof.

In some embodiments, provided herein is a method of preventing spontaneous miscarriage in an individual, the method comprising providing to the individual an effective amount of lymphocytes previously cultured with fibroblasts. In some embodiments, the lymphocytes are paternal lymphocytes. In other embodiments, the lymphocytes are not paternal lymphocytes. Lymphocytes used in the present disclosure may express one or more markers. In some embodiments, the lymphocytes express CD4. In some embodiments, the lymphocytes express a marker selected from the group consisting of: TNF-beta, interleukin-10, CD25, CD127, surface vimentin, FoxP3, IL-35 receptor, Fas ligand, ILT-3, PD-L1, TIM-3, progesterone receptor, and VEGF receptor. The lymphocytes may be PBMCs. The PBMCs may be substantially free from erythrocytes and/or polymorphonuclear leukocytes. The lymphocytes may be T-regulatory cells. The lymphocytes may be NK cells. The NK cells may express CD56.

In some embodiments, the lymphocytes and the fibroblasts were cultured with prostaglandin E2, an opioid receptor antagonist (e.g., naltrexone), vascular endothelial growth factor (VEGF), GM-CSF, or a combination thereof. In some embodiments, the lymphocytes were cultured under hypoxic conditions.

In some aspects, fibroblasts and/or lymphocytes are provided to the individual together with an effective amount of granulocyte-macrophage colony-stimulating factor (GM-CSF). The GM-CSF may be provided substantially simultaneously with the fibroblasts and/or lymphocytes. The GM-CSF and the fibroblasts and/or lymphocytes may be provided sequentially. In some embodiments, the GM-CSF is provided at a dose of between 0.1 µg/kg and 100 µg/kg. In some embodiments, the GM-CSF is provided at a dose of about 1 µg/kg.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWING

For a more complete understanding of the present disclosure, reference is now made to the following descriptions taken in conjunction with the accompanying drawing.

FIG. 1 shows reduction in spontaneous resorptions is seen in mice receiving syngeneic, allogeneic or xenogeneic fibroblasts, compared to control (saline).

DETAILED DESCRIPTION

I. Examples of Definitions

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

A variety of aspects of this disclosure can be presented in a range format. It should be understood that the description in range format is merely for convenience and brevity and should not be construed as an inflexible limitation on the scope of the present disclosure. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges may include the range endpoints.

The term "subject," as used herein, may be used interchangeably with the term "individual" and generally refers to an individual in need of a therapy. The subject can be a mammal, such as a human, dog, cat, horse, pig or rodent. The subject can be a patient, e.g., have or be suspected of having or at risk for having a disease or medical condition related to bone. For subjects having or suspected of having a medical condition directly or indirectly associated with bone, the medical condition may be of one or more types. The subject may have a disease or be suspected of having the disease. The subject may be asymptomatic. The subject may be of any gender. The subject may be of a certain age, such as at least 30, 35, 40, 45, 50, 55, 60, 65, 70, 75, 80, 85, 90, 95, or 100 or more.

II. Methods and Compositions for Preventing Recurrent Miscarriage

Embodiments of the disclosure include methods of preventing miscarriages of any kind, including spontaneous miscarriages, in an individual, by providing to the individual an effective amount of fibroblasts and/or lymphocytes previously cultured with fibroblasts.

Without wishing to be bound by theory, it is believed that spontaneous abortion and recurrent spontaneous abortion are caused by or associated with inappropriate immune responses in a pregnant subject. In particular, it is believed that subjects at risk for spontaneous abortion possess inappropriate immune cytokines associated with T-helper 1 (Th1) and Th17 immune responses known to those of skill in the art. In contrast, subjects that have healthy pregnancies typically present immune cytokines associated with a T-helper 2 (Th2) immune response. It is believed that administration of G-CSF can reduce the inappropriate Th1 response and/or increase a T-helper 2 (Th2) immune response in a subject. This invention is thus based, in part, on the discovery that administration of fibroblasts, as well as fibroblast cultured lymphocytes, can shift a subject's immune response towards a healthy Th2 response during pregnancy and thereby reduce or eliminate the risk of spontaneous abortion.

Methods of the disclosure relate to immune modulatory therapy for prevention of miscarriage. Provided herein is the use of fibroblasts and cells that have been treated by (e.g., cultured with) fibroblasts as a cellular therapy to prevent recurrent miscarriages. Fibroblasts may be maternal fibroblasts. Cells treated with fibroblasts may be lymphocytes (e.g., paternal lymphocytes).

Disclosed here, in some embodiments, are means, methods and compositions useful for preventing immunologically mediated miscarriages. In one embodiment the disclosure encompasses the augmentation of immune modulatory properties of lymphocyte infusions by culture of said cells with maternally derived fibroblasts. In another embodiment, the disclosure teaches immune modulation in a subject predisposed for recurrent miscarriages through the administration of fibroblasts with ability to inhibit inflammatory and/or Th1 and/or Th17 responses. In one embodiment, administration of fibroblasts, and/or fibroblast-educated lymphocytes, is performed to reduce Th9 immunity and thus overcome propensity of the subject for pregnancy loss.

The subject can be any mammalian subject at risk for a spontaneous abortion. In some embodiments, the subject is a human female. In certain embodiments, the subject has previously had one or more spontaneous abortions. In further embodiments, the subject has previously had two or more spontaneous abortions. In other embodiments, the subject has had recurrent spontaneous abortions, i.e., three or more spontaneous abortions. In further embodiments, the subject can be any subject in a population at risk for spontaneous abortion. For instance, the subject can be a human female in an age group at risk for spontaneous abortion. In particular embodiments, the subject can be a human female greater than 35 years of age, greater than 40 years of age, or greater than 45 years of age. In other particular embodiments, the subject can be a human female less than 20 years of age or less than 15 years of age. However, essentially a woman of any age that presents with a reproductive infirmity, such as spontaneous abortion, preeclampsia and preterm labor, is a candidate for obtaining the materials and methods of the disclosure.

In further embodiments, the subject can also be in any other population at risk for spontaneous abortion as determined by a practitioner of skill in the art. In certain embodiments, the subject is threatening abortion. In other embodiments, the subject is obese, morbidly obese, has overall poor health or comorbid conditions that indicate a risk of spontaneous abortion to the skilled practitioner. In certain embodiments, these conditions can be incompetent cervix, uterine anomalies, hypothyroidism, diabetes mellitus, chronic nephritis, acute infection, use of illicit drugs, immunologic problems, severe emotional shock and viral infection (e.g., cytomegalovirus, herpes virus, and/or rubella). In certain embodiments, the subject has had an implantation failure during a previous assisted reproduction procedure.

Other subjects at risk include those with unusually high Th1 immune responses or unusually low Th2 immune responses.

In some embodiments, females are identified who may benefit from an immune modulatory therapy. Identification of females who may benefit from an immune modulatory therapy may involve screening for individuals who have had more than three consecutive miscarriages and possess elevated levels of inflammatory markers such as inflammatory cytokines.

In some embodiments, fibroblast cells used in the disclosed methods may be capable of proliferating and differentiating into ectoderm, mesoderm, or endoderm. In some embodiments, fibroblast cells express at least one of Oct-4, Nanog, Sox-2, KLF4, c-Myc, Rex-1, GDF-3, LIF receptor, CD105, CD117, CD344 or Stella markers. In some embodiments, fibroblast cells do not express at least one of MHC class I, MHC class II, CD45, CD13, CD49c, CD66b, CD73, CD105, or CD90 cell surface proteins.

Fibroblast cells may be expanded and utilized by administration themselves, or may be cultured in a growth media for expansion and/or stimulation of lymphocytes. The term Growth Medium generally refers to a medium sufficient for the culturing of fibroblasts. In particular, one presently preferred medium for the culturing of the cells of the invention herein comprises Dulbecco's Modified Essential Media (also abbreviated DMEM herein). Particularly preferred is DMEM-low glucose (also DMEM-LG herein) (Invitrogen®, Carlsbad, Calif.). The DMEM-low glucose is preferably supplemented with 15% (v/v) fetal bovine serum (e.g. defined fetal bovine serum, Hyclone™, Logan, Utah), antibiotics/antimycotics (preferably penicillin (100 Units/milliliter), streptomycin (100 milligrams/milliliter), and amphotericin B (0.25 micrograms/milliliter), (Invitrogen®, Carlsbad, Calif.)), and 0.001% (v/v) 2-mercaptoethanol (Sigma®, St. Louis Mo.). In some cases different growth media are used, or different supplementations are provided, and these are normally indicated in the text as supplementations to Growth Medium. Also relating to the present invention, the term standard growth conditions, as used herein, refers to culturing of cells at 37° C., in a standard atmosphere comprising 5% $CO_2$, where relative humidity is maintained at about 100%. While the foregoing conditions are useful for culturing, it is to be understood that such conditions are capable of being varied by the skilled artisan who will appreciate the options available in the art for culturing cells, for example, varying the temperature, $CO_2$, relative humidity, oxygen, growth medium, and the like.

Fibroblast cells used in the disclosed methods can undergo at least 25, 30, 35, or 40 doublings prior to reaching a senescent state. Methods for deriving cells capable of doubling to reach $10^{14}$ cells or more are provided. Preferred are those methods which derive cells that can double sufficiently to produce at least about $10^{14}$, $10^{15}$, $10^{16}$, or $10^{17}$ or more cells when seeded at from about $10^3$ to about $10^6$ cells/cm$^2$ in culture. Preferably these cell numbers are produced within 80, 70, or 60 days or less. In one embodiment, fibroblast cells are isolated and expanded, and possess one or more markers selected from a group consisting of CD10, CD13, CD44, CD73, CD90, CD141, PDGFr-alpha, HLA-A, HLA-B, or HLA-C. In some embodiments, the fibroblast cells do not produce one or more of CD31, CD34, CD45, CD117, CD141, HLA-DR, HLA-DP, or HLA-DQ.

In some cases, fibroblast cells are obtained from a biopsy, and the donor providing the biopsy may be either the individual to be treated (autologous), or the donor may be different from the individual to be treated (allogeneic). In cases wherein allogeneic fibroblast cells are utilized for an individual, the fibroblast cells may come from one or a plurality of donors. In some embodiments, fibroblast cells used in the disclosed methods are maternal fibroblasts.

The fibroblasts may be obtained from a source selected from the group consisting of: dermal fibroblasts; placental fibroblasts; adipose fibroblasts; bone marrow fibroblasts; foreskin fibroblasts; umbilical cord fibroblasts; hair follicle derived fibroblasts; nail derived fibroblasts; endometrial derived fibroblasts; keloid derived fibroblasts; and a combination thereof.

In some embodiments, an effective amount of fibroblast cells are provided to an individual to prevent spontaneous miscarriage in the individual. In some embodiments, lymphocytes are cultured with fibroblasts, and an effective amount of the lymphocytes are provided to an individual to prevent spontaneous miscarriage in the individual. Administration of the fibroblasts cells and/or lymphocytes to the individual may be performed in agreement with standard practices that are known to one skilled in the art. Example routes of administration of fibroblasts and/or lymphocytes include parenteral (e.g., intravenous, intradermal, microvascular bed of bone marrow, subcutaneous), oral (e.g., ingestion or inhalation), transdermal (e.g., topical), transmucosal, and rectal administration. In certain particular aspects, cells are administered from a route selected from a group consisting of: intravenously, intraarterially, intramuscularly, subcutaneously, transdermally, intratracheally, intraperitoneally, intravitreally, and via direct injection into bone compartments or into spinal fluid. In some aspects, the cells, compositions or other materials can be provided with a scaffolding support. In certain aspects, the cells are administered in or proximal to the placenta. In certain aspects, the homing and engraftment of the fibroblasts and/or lymphocytes takes place within the placenta of the individual in need thereof. In certain aspects, the cells are administered by multiple routes and/or sites, either simultaneously or sequentially.

In certain embodiments, the cells are administered to the subject prior to pregnancy. For instance, the cells may be administered to a subject that is planning or attempting to become pregnant. In other embodiments, the cells are administered to a pregnant subject. The cells can be administered at any time during the first or second trimester of pregnancy. In preferred embodiments, the cells are administered during the first 20 weeks of pregnancy.

Numerous studies have demonstrated that RSA is associated with increased production of Th1 cytokines such as interferon gamma and reduced production of IL-10. Furthermore, treatments that have demonstrated some signal of efficacy in RSA such as IVIG, G-CSF, and PLT, all have been shown to induce a Th1 to Th2 shift. Within the context of the current disclosure, use of fibroblast and cell mixtures, particularly adipose fibroblast cells for inducing immune modulation towards protecting the fetal allograft, are envisioned. In one specific embodiment, stromal vascular fraction (SVF) from adipose tissue is used to extract autologous fibroblast cells, which are expanded and administered into a mammal suffering from RSA at a concentration sufficient to evoke a therapeutic response. Such concentrations may be determined by monitoring natural killer (NK) cell activity, assessing inflammatory cytokine production by peripheral blood mononuclear cells after stimulation with a mitogen or mitogenic antibody, or by assessment of T regulatory (Treg) cell numbers or activity. In one embodiment RSA patients are administered the autologous SVF derived fibroblasts at a concentration of 50 million cells, once per month.

In some embodiments, fibroblasts and/or lymphocytes conditioned by fibroblasts are administered together with immune modulatory drugs in order to augment suppression of abortogenic cytokines. One immune modulatory drug that is useful for combination with the fibroblasts and/or lymphocytes of the present disclosure is GM-CSF. In one embodiment, the patient receiving fibroblasts and/or lymphocytes conditioned by fibroblasts is administered daily doses of GM-CSF is 0.1 μg/kg to 100 μg/kg. In some embodiments, said daily administered dose is about 1 μg/kg. In another embodiment, GM-CSF is administered every day from the day of ovulation until the ninth week of pregnancy. In another embodiment, human chorionic gonadotropin (hCG) is administered to enhance immune modulation.

For administration of GM-CSF, one of skill in the art may consult various clinically available protocols involving GM-CSF. For example, Leukine® is the registered trade name of sargramostim, recombinant GM-CSF produced by yeast cells, developed by Immunex (now Amgen®), administered for the first time in 1987, as part of a compassionate-use protocol, to six men who were victims of radioactive cesium contamination following the accident which occurred in Goiania. It is currently produced by Berlex Laboratories, a subsidiary of Schering AG. Its use is currently approved both in the USA and in Europe for treatment following autologous bone marrow transplantation in patients with myeloproliferative pathologies such as non-Hodgkin's lymphoma, acute lymphocytic leukemia or Hodgkin's disease. Moreover, in 1996 the FDA approved the use of sargramostim for the treatment of fungal infections and the treatment of post-chemotherapy aplastic anemia. A study which was published in 2005 in the New England Journal of Medicine concluded that GM-CSF promotes a significant increase in remissions in patients suffering from Crohn's disease with a reduction in the severity of the illness and improvement in the quality of life. GM-CSF has also been tested for the treatment of patients suffering from Alzheimer's disease, for demyelinating diseases such as multiple sclerosis, for treatment and revascularization in myocardial infarction and for the treatment of cerebral thrombosis, with encouraging results.

III. Methods for Pregnancy Complication Risk Evaluation

Embodiments of the present disclosure are directed to methods and systems for identification of inflammatory and immunological abnormalities in order to categorize risk of pregnancy complications. Said pregnancy complications may be defined as medical incidences that threaten the health of the mother or the offspring, and may include recurrent early spontaneous abortion (RESA), preterm birth, pre-eclampsia including hemolysis, elevated liver enzymes low platelets (HELP), premature rupture of the membrane, antepartum hemorrhage including placental abruption, chorioamnionitis, Intrauterine growth restriction, placenta pravaevia, and sequalae of intraamniotic infection.

In some embodiments, levels of circulating factors are assessed in maternal plasma and, based on abnormally high levels, interventions are chosen for treatment. In one particular embodiment, assessment of circulating IL-6 is utilized as a marker of risk for pregnancy complications. Specifically, plasma is analyzed in the first trimester of pregnancy and concentrations correlated with a baseline associated with non-complicated pregnancy. Within the context of the disclosure, other markers of inflammation may be utilized such as C reactive protein, IL-1, TNF-alpha, and IL-18. In females who have higher concentration of inflammatory proteins as compared to baseline values from non-complicated pregnancies, an agent may be administered to reduce inflammation. For example, fibroblasts (e.g., maternal fibroblasts) and/or lymphocytes cultured with fibroblasts may be provided to the female, thereby reducing the risk of pregnancy complications such as spontaneous miscarriage.

EXAMPLES

The following examples are included to demonstrate particular embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Syngeneic, Allogeneic, and Xenogeneic Fibroblasts Prevent Recurrent Spontaneous Abortion in the CbaxDba/2

The established CBA×DBA/2 mouse model of immunologically mediated spontaneous abortion [3], was utilized to assess effects of fibroblast administration on resorption at day 15 of murine pregnancy.

Syngeneic CBA fibroblasts, allogeneic DBA/2 fibroblasts, and human fibroblasts were isolated from skin punch biopsy, collagenase digested, and expanded in OptiMEM media with 10% fetal calf serum.

Wild type 8-10 week old virgin CBA/J female mice and 8-14 week old DBA/2J male mice were paired and vaginal plug was assessed two times a day. Day of formation of the vaginal plug was designated as day zero of pregnancy. Ten pregnant female mice were intravenously administered 500,000 syngeneic (CBA), allogeneic (DBA/2) or xenogeneic (human). Another 10 mice were used as controls and treated with saline. Administration of cells was performed on day 3 of pregnancy, when animals were sacrificed and uterine horns were examined for presence of resorbed offspring. Resorption was expressed as number of resorptions/total number of formed fetuses and resorptions.

As seen in FIG. 1, a significant reduction in spontaneous resorptions is seen in mice receiving syngeneic, allogeneic or xenogeneic fibroblasts.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

1. [0009] Gatenby P A, Cameron K, Simes R J. Treatment of recurrent spontaneous abortion by immunization with paternal lymphocytes: results of a controlled trial. Am J Reprod Immunol. 1993 March; 29(2): 88-94

2. [0010] Recurrent Pregnancy Losses and the Role of Immunotherapy. Review Article, Arch Gynecol Obstet (2000) 264:3-12

3. [0011] Bonney, E. A. and S. A. Brown, *To drive or be driven: the path of a mouse model of recurrent pregnancy loss*. Reproduction, 2014. 147(5): p. R153-67.

What is claimed is:

1. A method of preventing spontaneous miscarriage in an individual, the method comprising providing to the individual an effective amount of fibroblasts.

2. The method of claim 1, wherein:
  (a) peripheral blood mononuclear cells (PBMCs) from the individual have increased interleukin-18 expression relative to a control or healthy individual;
  (b) PBMCs from the individual have increased interferon gamma expression relative to a control or healthy individual;
  (c) PBMCs from the individual have increased TNF-alpha expression relative to a control or healthy individual;
  (d) PBMCs from the individual have increased natural killer cell activity relative to a control or healthy individual.

3. The method of claim 1, wherein the individual has a reduced T regulatory cell activity relative to a control or healthy individual.

4. The method of claim 1, wherein, prior to the providing, the fibroblasts are cultured with one or more mitogenic factors.

5. The method of claim 1, wherein, prior to the providing, the fibroblasts are cultured under hypoxic conditions.

6. The method of claim 1, wherein the fibroblasts express a marker selected from the group consisting of Oct-4, Nanog, Sox-2, KLF4, c-Myc, Rex-1, GDF-3, LIF receptor, CD105, CD117, CD344, Stella, and a combination thereof and/or wherein the fibroblasts do not express a marker selected from the group consisting of MHC class I, MHC class II, CD45, CD13, CD49c, CD66b, CD73, CD 105, CD90, and a combination thereof.

7. The method of claim 1, further comprising providing to the individual an effective amount of granulocyte-macrophage colony-stimulating factor (GM-CSF).

8. The method of claim 1, further comprising culturing the fibroblasts prior to providing the fibroblasts to the individual.

9. The method of claim 8, wherein the fibroblasts are cultured with one or more growth factors.

10. The method of claim 8, wherein the one or more growth factors comprise IGF, EGF, VEGF, FGF-1, FGF-2, FGF-5, TGF-beta, oxytocin, GDF-11, or a combination thereof.

11. The method of claim 8, wherein the fibroblasts are cultured with one or more immune modulating agents.

12. The method of claim 11, wherein the one or more immune modulating agents comprise interferon gamma, interferon beta, interferon alpha, TNF-a, IL-10, IL-35, or a combination thereof.

13. A method of preventing spontaneous miscarriage in an individual, the method comprising providing to the individual an effective amount of lymphocytes previously cultured with fibroblasts.

14. The method of claim 13, wherein the lymphocytes are paternal lymphocytes.

15. The method claim 14, wherein the lymphocytes express CD4.

16. The method of claim 13, wherein the lymphocytes express a marker selected from the group consisting of: TNF-beta, interleukin-10, CD25, CD127, surface vimentin, FoxP3, IL-35 receptor, Fas ligand, ILT-3, PD-L1, TIM-3, progesterone receptor, VEGF receptor, and a combination thereof.

17. The method of claim 13, wherein the lymphocytes are PBMCs, T-regulatory cells, or are natural killer cells.

18. The method of claim 17, wherein the PBMCs are substantially free from erythrocytes and/or polymorphonuclear leukocytes.

19. The method of claim 17, wherein the natural killer cells express CD56.

20. The method of claim 13, wherein the lymphocytes and the fibroblasts were:
   (a) cultured with prostaglandin E2;
   (b) cultured with one or more opioid receptor antagonists;
   (c) cultured with VEGF;
   (d) cultured with GM-CSF;
   (e) cultured under hypoxic conditions.

21. The method of claim 13, further comprising providing to the individual an effective amount of GM-CSF.

22. The method of claim 1, wherein the fibroblasts are syngeneic, allogeneic or xenogeneic with respect to the individual.

* * * * *